(12) United States Patent
Ohtsuki

(10) Patent No.: US 6,973,161 B2
(45) Date of Patent: Dec. 6, 2005

(54) X-RAY FOREIGN MATERIAL DETECTING APPARATUS SIMULTANEOUSLY DETECTING A PLURALITY OF X-RAYS HAVING DIFFERENT AMOUNTS OF ENERGY

(75) Inventor: Tomoyasu Ohtsuki, Yokohama (JP)

(73) Assignee: Anritsu Industrial Solutions Co., Ltd., Atsugi (JP)

( * ) Notice: Subject to any disclaimer, the term of this patent is extended or adjusted under 35 U.S.C. 154(b) by 103 days.

(21) Appl. No.: 10/153,324

(22) Filed: May 22, 2002

(65) Prior Publication Data

US 2002/0181652 A1    Dec. 5, 2002

(30) Foreign Application Priority Data

Jun. 4, 2001    (JP) ............................ 2001-168398

(51) Int. Cl.[7] .......................................... G01N 23/04
(52) U.S. Cl. ................ 378/57; 378/5; 378/53
(58) Field of Search ................ 378/57, 53, 5

(56) References Cited

U.S. PATENT DOCUMENTS 5,040,199 A * 8/1991 Stein ........................ 378/56
5,490,218 A   2/1996 Krug et al.

FOREIGN PATENT DOCUMENTS

| JP | 1-026132 A | 1/1989 |
|----|----|----|
| JP | 10-318943 A | 12/1998 |
| JP | 11-231056 A | 8/1999 |
| JP | 2001-133554 A | 5/2001 |

* cited by examiner

Primary Examiner—Craig E. Church
(74) Attorney, Agent, or Firm—Frishauf, Holtz, Goodman & Chick, P.C.

(57) ABSTRACT

A conveying section conveys an inspected object so as to cross the X-rays irradiated from an X-ray generating section. A first sensor module is disposed along a transmitting direction of the X-rays transmitted through the inspected object, and receives one portion of the X-rays transmitted through the inspected object, and outputs a first electric signal corresponding to a first X-ray energy amount. A second sensor module receives a remaining portion of the X-rays transmitted through the inspected object, and outputs a second electric signal corresponding to a second X-ray energy amount different from the first X-ray energy amount. Presence/absence of a foreign material mixed in the inspected object can be detected based on the first and second electric signals, which are output from the first and second sensor modules to the same inspected object at substantially the same detection time.

4 Claims, 5 Drawing Sheets

→ X-rays
---→ Visible light

X-RAY FOREIGN MATERIAL DETECTING APPARATUS SIMULTANEOUSLY DETECTING A PLURALITY OF X-RAYS HAVING DIFFERENT AMOUNTS OF ENERGY

CROSS-REFERENCE TO RELATED APPLICATIONS

This application is based upon and claims the benefit of priority from the prior Japanese Patent Application No. 2001-168398, filed Jun. 4, 2001, the entire contents of which are incorporated herein by reference.

BACKGROUND OF THE INVENTION

1. Field of the Invention

The present invention relates to an X-ray foreign material detecting apparatus, and to an X-ray foreign material detecting apparatus for detecting a foreign material (a foreign body or a foreign material, hereinafter called a foreign material) in an inspected object from a transmitted amount of X-rays at the time of irradiating X-rays onto various types of inspected objects such as raw meat, fish, processed food, and medicine.

2. Description of the Related Art

Conventionally, for example, an X-ray foreign material detecting apparatus is used in order to detect a foreign material (metal, bone, glass, stone, synthetic resin material, or the like) mixed in (including at the surface of) an inspected object such as raw meat, fish, processed food, and medicine.

FIG. 5 is a schematic diagram showing a structure of this type of X-ray foreign material detecting apparatus conventionally known.

As shown in FIG. 5, in the conventional X-ray foreign material detecting apparatus, an X-ray generating section 50 is mounted at the upper side, and an X-ray detecting section 51 is mounted at the lower side.

Further, in the X-ray foreign material detecting apparatus, X-rays irradiated from the X-ray generating section 50 pass through an inspected object W, such as described above, and thereafter, are received at the X-ray detecting section 51.

In this case, a conveying section 52 for conveying the inspected object W in X-rays irradiated from the X-ray generating section 50, is mounted on the X-ray foreign material detecting apparatus body.

In this way, due to the X-ray foreign material detecting apparatus irradiating X-rays onto the inspected object W conveyed on the conveying section 52 and the transmitted X-rays transmitted through the inspected object W being received at the X-ray detecting section 51, whether or not a foreign material is mixed in the inspected object W is detected.

In such a conventional X-ray foreign material detecting apparatus, the X-ray generating section 50 and the X-ray detecting section 51 are single, and form a pair.

In this way, because the radiation quality (the length of the wavelength, i.e., the magnitude of the amount of energy) of the X-rays irradiated from the X-ray generating section 50 is single, the properties of the foreign material which can be detected by such X-rays are limited.

Concretely, when a foreign material is mixed in a processed food, if the foreign material is metal or the like whose composition is different from that of the processed food and which has a high X-ray absorption rate, the foreign material can be detected relatively easily.

However, if the output or the radiation quality of the X-rays is set to detect metal, when a foreign material such as bone, shell or the like whose composition or X-ray absorption rate is substantially the same as that of the processed food is mixed in, it is difficult to detect it.

Further, if the output or the radiation quality of the X-rays is set to detect metal as described above, it is difficult to detect a small foreign material or a thin foreign material mixed in the inspected object W.

In order to solve the problems described above, conventionally, an X-ray foreign material detecting apparatus structured such that a plurality of X-rays are irradiated onto the inspected object W has been considered, and for example, has been disclosed in Jpn. Pat. Appln. KOKAI Publication No. 10-318943 and the like.

As shown in FIG. 6, the improved X-ray foreign material detecting apparatus has a structure in which, in addition to the above-described pair of the X-ray generating section 50 and the X-ray detecting section 51, another pair of an X-ray generating section 60 and an X-ray detecting section 61 is provided on the conveying direction of the conveying section 52.

In the conventional X-ray foreign material detecting apparatus structured in this way, an X-ray filter 62 is disposed within the X-rays irradiated from the X-ray generating section 60 so as to reach the X-ray detecting section 61.

Due to the X-ray filter 62, the radiation quality of the X-rays from the X-ray generating section 60 can be made to be different from the radiation quality of the X-rays from the X-ray generating section 50.

In this way, a foreign material which is different from a foreign material detected at the X-ray detecting section 51 can be detected at the X-ray detecting section 61.

By image processing the detection signals of these X-ray detecting sections 51, 61 respectively at an X-ray detection signal processing section (not shown), more detailed foreign material detection, such as the image of the foreign material emphasized on the basis of both the detection signals or the like, can be carried out. Thus, it is possible to aim for more accurate detection of foreign materials.

The X-ray detecting sections 51, 61 are respectively structured by line sensors disposed at different positions in a direction orthogonal to the conveying direction of the conveying section 52.

The line sensor is formed from a scintillator converting the X-rays into light, and a photodiode array receiving the light converted at the scintillator.

However, in the above-described structure, the two pairs of the X-ray generating sections 50, 60 and the X-ray detecting sections 51, 61 are needed. Thus, there are problems that the costs are high, and because much larger placement space is required, it leads to the entire apparatus becoming larger.

Note that Jpn. Pat. Appln. KOKAI Publication No. 10-318943 also discloses an X-ray foreign material detecting apparatus for irradiating X-rays from a single X-ray generating portion and detecting transmitted X-rays transmitted through the inspected object W, at the two X-ray detecting sections 51, 61 disposed at respectively different positions on the conveying direction of the conveying section 52.

In this case, the X-ray filter 62 is provided at one of the X-ray detecting sections 51, 61.

In an X-ray foreign material detecting apparatus in accordance with this structure, it suffices to use one X-ray generating section and the two X-ray detecting sections 51, 61. Thus, as compared with the X-ray foreign material detecting apparatus in accordance with the above-described structure, it is somewhat advantageous in terms of cost and space, but there is a problem that it is not that marked an improvement.

FIGS. 7A, 7B, and 7C are views showing X-ray transmitted images of the inspected object W in an X-ray detection signal processing section (not shown) based on a plurality of detection signals, in accordance with the conventional X-ray foreign material detecting apparatus having the above-described plural X-ray irradiating structure.

FIG. 7A shows an X-ray transmitted image A at the X-ray detector 51 side in the X-ray detection signal processing section (not shown).

Further, FIG. 7B shows an X-ray transmitted image B at the X-ray detector 61 side in the X-ray detection signal processing section (not shown).

Moreover, FIG. 7C shows a superposed image of the aforementioned X-ray transmitted images A, B in the X-ray detection signal processing section (not shown).

As described above, in the X-ray foreign material detecting apparatus structured so as to irradiate a plurality of X-rays, in any case, the X-ray detecting sections 51, 61 are disposed at different positions on the conveying direction of the conveying section 52. Thus, the detection time differs even for the same inspected object W.

Accordingly, when both images A, B are merely superposed in the X-ray detection signal processing section (not shown), as shown in FIG. 7C, images of the inspected object W and a foreign material G are offset by a distance L (corresponding to time as well), and a problem arises in that superposition processing cannot be carried out in that state.

In order to correct this time lag, in the X-ray detection signal processing section (not shown), special processing, such as signal delaying, is required.

Further, FIGS. 8A, 8B, and 8C are views showing another example of X-ray transmitted images of the inspected object W in an X-ray detection signal processing section (not shown) based on a plurality of detection signals, in accordance with a conventional X-ray foreign material detecting apparatus having the above-described plural X-ray irradiating structure.

FIG. 8A shows an X-ray transmitted image A at the X-ray detector 51 side in the X-ray detection signal processing section (not shown).

Further, FIG. 8B shows an X-ray transmitted image B at the X-ray detector 61 side in the X-ray detection signal processing section (not shown).

Moreover, FIG. 8C shows a superposed image of the aforementioned X-ray transmitted images A, B in the X-ray detection signal processing section (not shown).

When the inspected object W is retort pack food or the like, the configuration may change during the conveying by the conveying section 52.

In the example shown in FIGS. 8A, 8B, and 8C, when detection is carried out by each of the X-ray detectors 51, 61, the configuration of the inspected object W changes.

When the configuration of the inspected object W varies in this way, at the X-ray detection signal processing section (not shown), the superposition processing itself of both the images cannot be carried out.

In this way, in a structure in which only the X-ray generating section and the X-ray detecting section are disposed along the conveying section 52, the accuracy of detection of foreign material by X-rays cannot be improved.

In particular, in various types of production lines, when detecting whether or not foreign material is mixed in inspected objects W manufactured successively, determination of the detection of foreign material must be carried out in real time. Obtaining both high-speed and highly-accurate foreign material detection is desired.

BRIEF SUMMARY OF THE INVENTION

In order to solve the above-described problem, an object of the present invention is to provide an X-ray foreign material detecting apparatus capable of achieving high-speed and highly-accurate foreign material detection.

In order to achieve the above object, according to a first aspect of the present invention, there is provided an X-ray foreign material detecting apparatus comprising:

an X-ray generating section (1) which irradiates X-rays;

a conveying section (3) which conveys an inspected object (W) so as to cross the X-ray irradiated from the X-ray generating section;

a first sensor module (2a) which is disposed along a transmitting direction of the X-rays transmitted through the inspected object, receives one portion of the X-rays transmitted through the inspected object, and outputs a first electric signal corresponding to a first X-ray energy amount by using the one portion of the X-rays transmitted through the inspected object; and a second sensor module (2b) which receives a remaining portion of the X-rays transmitted through the inspected object, and outputs a second electric signal corresponding to a second X-ray energy amount different from the first X-ray energy amount by using the remaining portion of the X-rays transmitted through the inspected object, wherein presence/absence of a foreign material mixed in the inspected object can be detected on the basis of the first electric signal and the second electric signal, respectively corresponding to the first X-ray energy amount and the second X-ray energy amount different from the first X-ray energy amount, which are output from the first and second sensor modules to the same inspected object at substantially the same detection time.

According to a second aspect of the present invention, there is provided an X-ray foreign material detecting apparatus according to the first aspect, wherein at least one of the first and second sensor modules has an X-ray filter to make the first X-ray energy amount and the second X-ray energy amount be different from each other by a predetermined magnitude by using the one portion or the remaining portion of the X-rays transmitted through the inspected object.

According to a third aspect of the present invention, there is provided an X-ray foreign material detecting apparatus according to the first aspect, wherein the first sensor module has a first sensor device which is disposed at a predetermined position perpendicular to a conveying direction of the inspected object by the conveying section and which outputs the first electric signal corresponding to the first X-ray energy amount by using the one portion of the X-rays transmitted through the inspected object, and directs the remaining portion of the X-rays transmitted through the inspected object to the second sensor module along the transmitting direction of the X-rays.

According to a fourth aspect of the present invention, there is provided an X-ray foreign material detecting apparatus according to the third aspect, wherein the second sensor module has an X-ray filter which is disposed at a position corresponding to the predetermined position at which the first sensor module is disposed and which is to make the second X-ray energy amount be different from the first X-ray energy amount by a predetermined magnitude by using the remaining portion of the X-rays transmitted through the inspected object, the remaining portion being directed from the first sensor module to the second sensor module, and has a second sensor device which outputs the second electric signal corresponding to the second X-ray energy amount.

According to a fifth aspect of the present invention, there is provided an X-ray foreign material detecting apparatus according to the first aspect, wherein the first sensor module has a first scintillator which converts the one portion of the X-rays transmitted through the inspected object into a first light, and a first light-receiving element to receive the first light converted by the first scintillator and output the first electric signal corresponding to the first X-ray energy amount, and directs the remaining portion of the X-rays transmitted through the inspected object to the second sensor module along the transmitting direction of the X-rays.

According to a sixth aspect of the present invention, there is provided an X-ray foreign material detecting apparatus according to the fifth aspect, wherein the first sensor module has a light reflector which directs the first light converted by the first scintillator to the light-receiving element.

According to a seventh aspect of the present invention, there is provided an X-ray foreign material detecting apparatus according to the fifth aspect, wherein the second sensor module has an X-ray filter to make the second X-ray energy amount be different from the first X-ray energy amount by a predetermined magnitude by using the remaining portion of the X-rays transmitted through the inspected object, the remaining portion being directed from the first sensor module to the second sensor module, a second scintillator which converts the second X-ray energy amount, made different from the first X-ray energy amount by the predetermined magnitude by the X-ray filter, into a second light, and a second light-receiving element to receive the second light converted by the second scintillator and output the second electric signal corresponding to the second X-ray energy amount.

According to an eighth aspect of the present invention, there is provided an X-ray foreign material detecting method comprising:

irradiating X-rays;

conveying an inspected object (W) so as to cross the X-rays;

receiving one portion of the X-rays transmitted through the inspected object, and outputting a first electric signal corresponding to the first X-ray energy amount by using the one portion of the X-rays transmitted through the inspected object, by a first sensor module (2a) disposed along a transmitting direction of the X-rays transmitted through the inspected object; and receiving a remaining portion of the X-rays transmitted through the inspected object, and outputting a second electric signal corresponding to the second X-ray energy amount different from the first X-ray energy amount by using the remaining portion of the X-rays transmitted through the inspected object, by a second sensor module (2b), wherein presence/absence of a foreign material mixed in the inspected object can be detected on the basis of the first electric signal and the second electric signal, respectively corresponding to the first X-ray energy amount and the second X-ray energy amount different from the first X-ray energy amount, which are output from the first and second sensor modules to the same inspected object at substantially the same detection time.

According to a ninth aspect of the present invention, there is provided an X-ray foreign material detecting method according to the eighth aspect, further comprising:

making the first X-ray energy amount and the second X-ray energy amount be different from each other by a predetermined magnitude by using the one portion or the remaining portion of the X-rays transmitted through the inspected object, by an X-ray filter provided at at least one of the first and second sensor modules.

According to a tenth aspect of the present invention, there is provided an X-ray foreign material detecting method comprising:

irradiating X-rays;

conveying an inspected object so as to cross the X-rays;

converting one portion of the X-rays transmitted through the inspected object into a first light;

receiving the first light, and outputting a first electric signal corresponding to a first X-ray energy amount;

obtaining X-rays which have a second X-ray energy amount different from the first X-ray energy amount by a predetermined magnitude, by using a remaining portion of the X-rays transmitted through the inspected object;

converting the X-rays which have the second X-ray energy amount into a second light; and receiving the second light, and outputting a second electric signal corresponding to the second X-ray energy amount, wherein presence/absence of a foreign material mixed in the inspected object can be detected on the basis of the first electric signal and the second electric signal, respectively corresponding to the first X-ray energy amount and the second X-ray energy amount different from the first X-ray energy amount, which are output to the same inspected object at substantially the same detection time.

According to the above structure, the X-rays irradiated to the inspected object W from the X-ray generating section 1 are transmitted through the inspected object to be received at the X-ray detecting section 2.

The X-ray detecting section 2 comprises a plurality of sensor modules 2a, 2b disposed at the upper and lower positions along the transmitting direction of the X-rays. The sensor modules 2a, 2b output X-ray transmission data according to the X-ray transmission amount from the light-receiving elements 23, 33, respectively.

The sensor module 2a at the upper stage converts the X-rays into visible light by the scintillator 21 and then, reflects the light at the visible light reflector 22 so as to detect the X-ray transmission amount by the light-receiving element 23.

In the sensor module 2b at the lower stage, X-ray energy in a predetermined band is damped by the X-ray filter 30, the X-rays are converted into visible light by the scintillator 31 and then the X-ray transmission amount is detected by the light-receiving element 33.

The sensor modules 2a, 2b are horizontally disposed so as to receive a single X-ray beam, and can detect the inspected object W simultaneously.

Further, the X-ray filter 30 is provided so that the radiation quality of the X-rays received at each sensor module 2a, 2b can be changed and the foreign material G in the inspected object W can be emphasized.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiment of the invention, and together with the general description given above and the detailed description of the embodiment given below, serve to explain the principles of the invention.

DETAILED DESCRIPTION OF THE INVENTION

Figure 1:
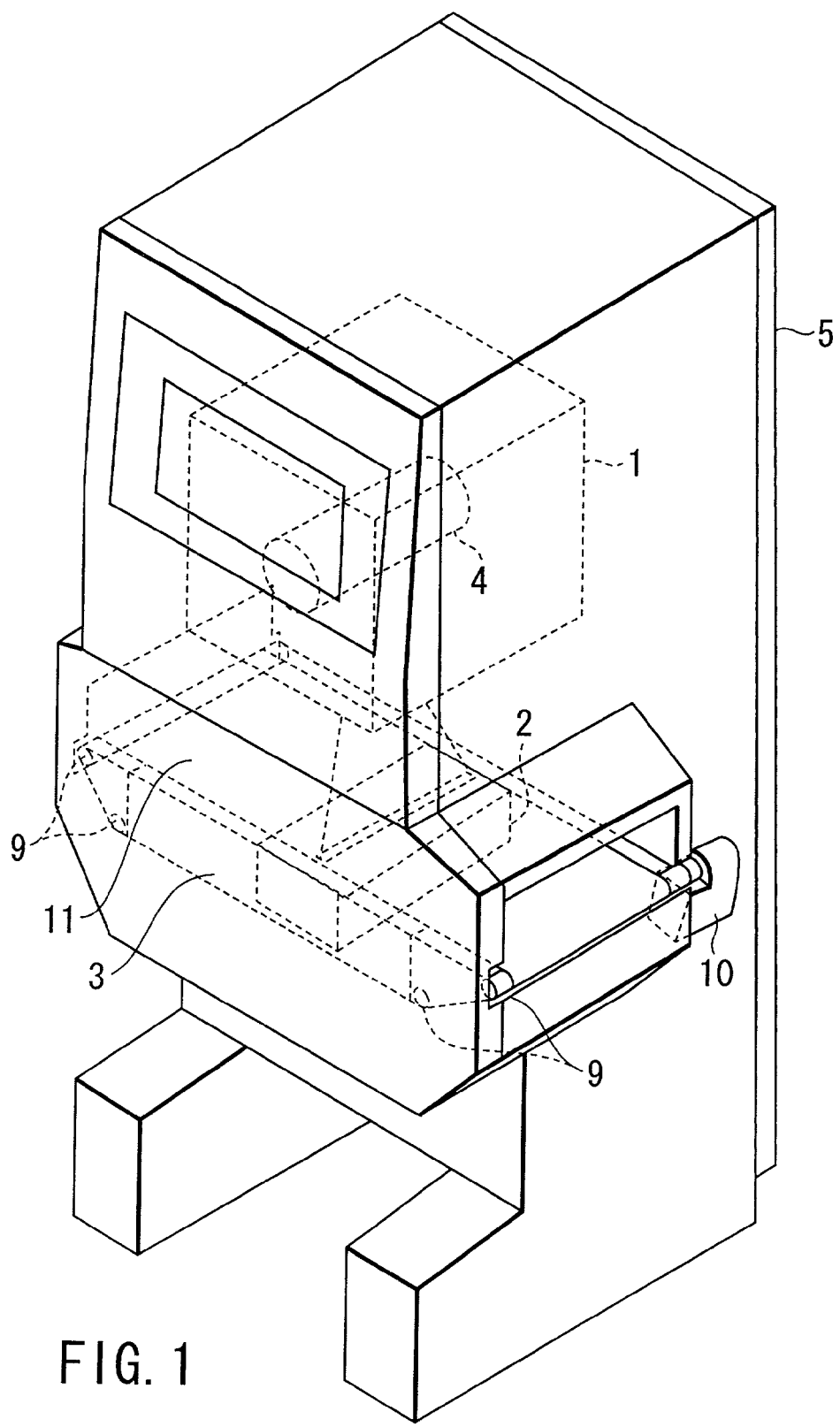
FIG. 1 is a perspective view showing an external structure of an X-ray foreign material detecting apparatus in accordance with a first embodiment of the present invention.

Reference will now be made in detail to the presently preferred embodiments of the invention as illustrated in the accompanying drawings, in which like reference numerals designate like or corresponding parts.

Hereinafter, several embodiments of the present invention will be described concretely and in detail with reference to the drawings.

(First Embodiment)

FIG. 1 is a perspective view showing an external structure of an X-ray foreign material detecting apparatus in accordance with a first embodiment of the present invention.

Namely, as shown in FIG. 1, the X-ray foreign material detecting apparatus in accordance with the first embodiment of the present invention is mainly comprised of an X-ray generating section 1 for generating X-rays, an X-ray detecting section 2 for receiving X-rays from the X-ray generating section 1, and a conveying section 3 for conveying an inspected object between the X-ray generating section 1 and the X-ray detecting section 2.

Firstly, the X-ray generating section 1 is structured so as to prevent the leakage of X-rays by covering the periphery of an X-ray tube 4 for generating X-rays with a shielding plate.

Here, the shielding plate is formed by shielding material such as lead, being lined on a storage section of the X-ray tube 4.

Further, the X-ray generating section 1 is disposed at the upper portion of a casing 5 forming the body of the X-ray foreign material detecting apparatus, and irradiates X-rays downward.

Note that X-rays, as shown by the alternate long and short dash lines, are irradiated in a substantially conical shape spreading downwardly from the X-ray tube 4.

Further, the X-ray generating section 1 is structured such that heat arising at the time of generating X-rays is dissipated by a cooling fin (not shown).

The X-ray detecting section 2 is disposed at a lower surface position of a conveying belt at an upper surface side of the conveying section 3. By receiving the X-rays irradiated in a substantially conical shape from the X-ray generating section 1, the X-ray detecting section 2 outputs an electric signal corresponding to the amount of energy of the received X-rays to a controlling means (not shown).

The X-ray detecting section 2 has a linear scintillator and an X-ray sensor which are housed in a metal box, and a slit formed to open at the upper surface of the metal box.

The slit is formed along the layout of the X-ray sensor, and constricts the substantially conical plane shaped X-rays irradiated from the X-ray generating section 1 into a linear form, and makes the X-rays pass through toward the X-ray sensor disposed in the metal box.

Figure 6:
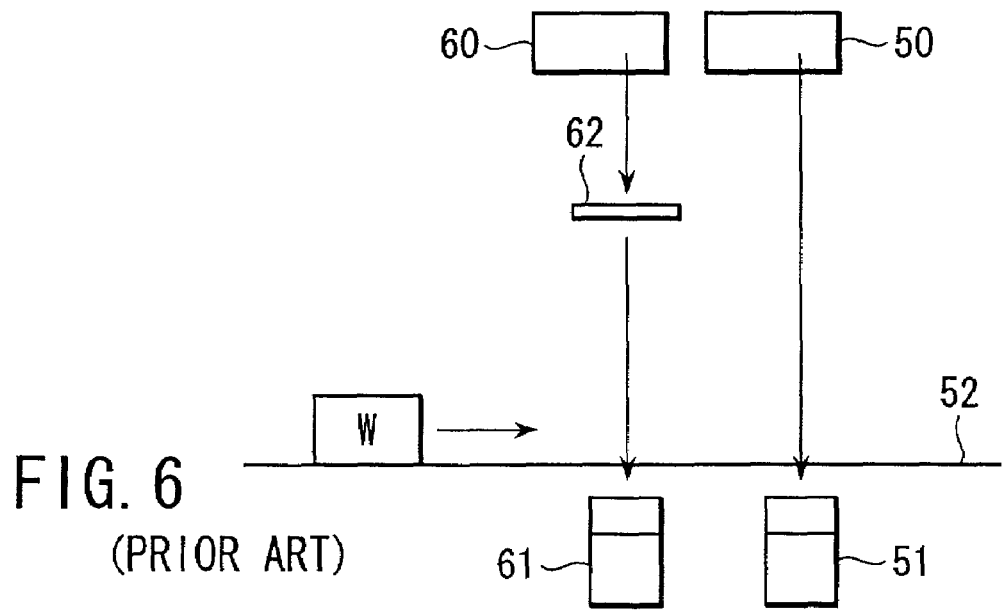
FIG. 6 is a schematic diagram showing a structure of a conventional improved X-ray foreign material detecting apparatus.
Figures 7A, 7B, 7C:
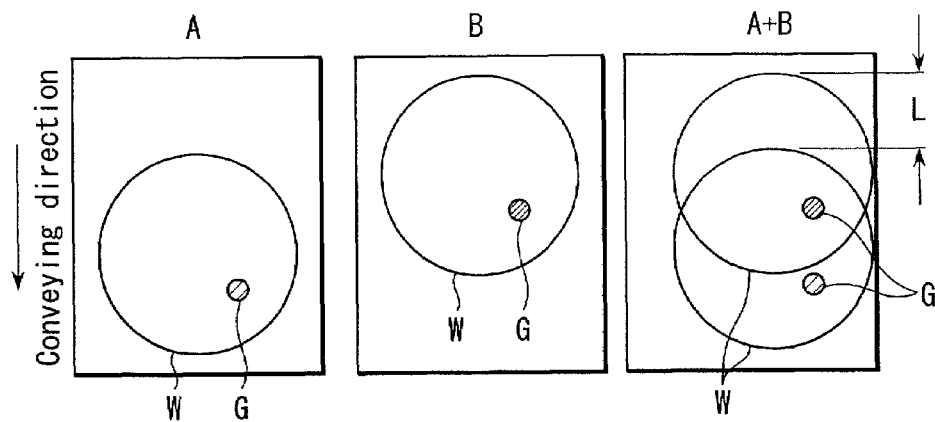
FIGS. 7A, 7B, and 7C are views showing one example of X-ray transmission images of an inspected object W at an X-ray detection signal processing section (not shown) based on a plurality of detection signals by a conventional X-ray foreign material detecting apparatus having a plural X-ray irradiating structure.
Figures 8A, 8B, 8C:
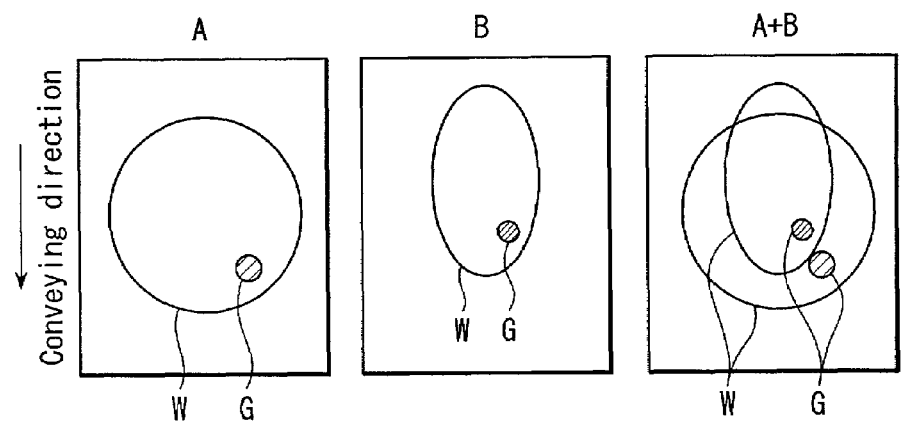
FIGS. 8A, 8B, and 8C are views showing another example of X-ray transmission images of an inspected object W at an X-ray detection signal processing section (not shown) based on a plurality of detection signals by the above-described conventional X-ray foreign material detecting apparatus having a plural X-ray irradiating structure.

Further, the conveying section 3 makes the inspected object W (refer to FIG. 1 and FIG. 6) pass so as to cross the X-ray portion irradiated from the X-ray generating section 1 toward the X-ray detecting section 2.

The conveying section 3 comprises rollers 9, a motor unit 10, and a conveyor belt 11.

Further, at the conveying section 3, the rollers 9 are rotated by driving of the motor unit 10, and the conveyor belt 11 is circulated in one direction.

The circulating direction of the conveyor belt 11 is a direction perpendicular to the direction of arrangement of the line sensor of the X-ray detecting section 2.

Figure 2:
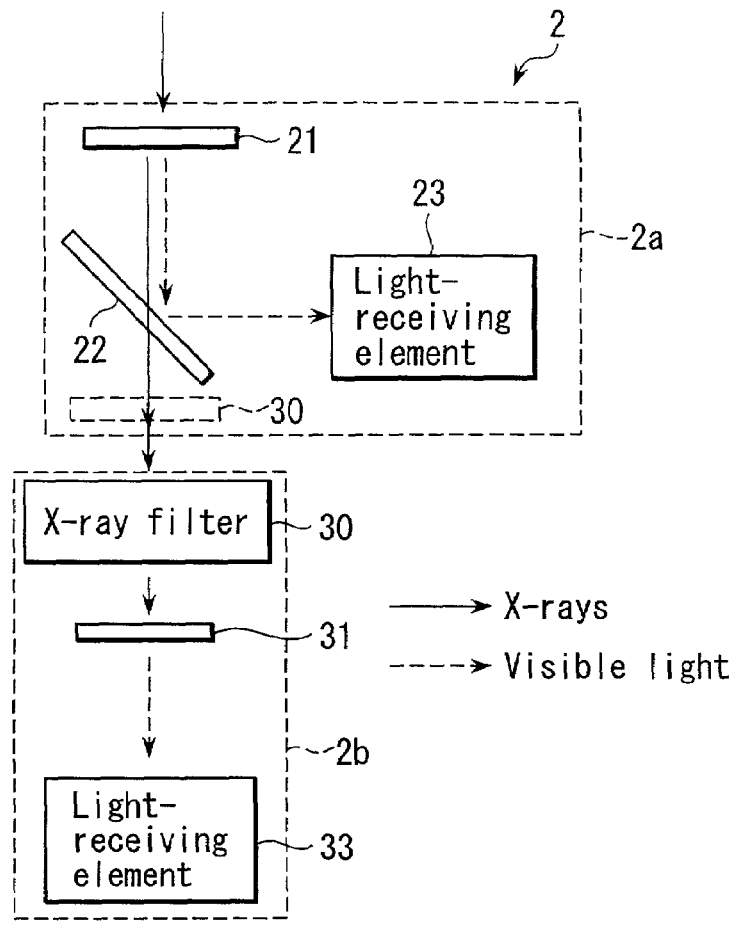
FIG. 2 is a diagram showing an inner structure of an X-ray detecting section 2 of FIG. 1, as a schematic diagram showing main portions of the X-ray foreign material detecting apparatus in accordance with the first embodiment of the present invention.

FIG. 2 is a diagram showing an inner structure of the X-ray detecting section 2 of FIG. 1, as a schematic diagram showing a structure of the main portions of the X-ray foreign material detecting apparatus in accordance with the first embodiment of the present invention.

Namely, as shown in FIG. 2, the X-ray detecting section 2 is structured from a plurality of sensor modules.

The X-ray detecting section 2 has a structure in which two sensor modules 2a, 2b are provided in the shown example.

These sensor modules 2a, 2b are disposed so as to be joined in the vertical direction so as to receive a single X-ray beam irradiated from the X-ray generating section 1 of FIG. 1.

The one sensor module 2a is provided at the upper stage, and the other sensor module 2b is provided at the lower stage.

Here, a scintillator 21, a visible light reflector 22, and a light-receiving element 23 are provided at the sensor module 2a at the upper stage.

Further, an X-ray filter 30, a scintillator 31, and a light-receiving element 33 are provided at the sensor module 2b at the lower stage.

In this case, the light-receiving elements 23, 33 are formed from a plurality of photodiodes arranged in linear form in the depthwise direction perpendicular to the surface of the drawing of FIG. 2.

Note that, the X-ray filter 30, the scintillators 21, 31, and the visible light reflector 22 also have predetermined lengths in the aforementioned depthwise direction along the arrangements of the light-receiving elements 23, 33.

Further, the visible light reflector 22 is formed from a whole reflection mirror, and is disposed so as to be inclined at an angle of 45° as shown in the drawing.

Further, the X-ray filter 30 is formed by a radiation quality variable body for varying the radiation quality of the X-rays (the wavelength band, i.e., the amount of energy).

The X-ray filter 30 is formed from a metal such as aluminum or copper, or carbon or a resin material, being formed in a thin plate form.

The X-ray filter 30 damps the amount of X-ray energy in a predetermined wavelength band received at the sensor module 2b.

This predetermined wavelength band can be set in accordance with the material and the like to be used for the X-ray filter 30.

In this way, at the sensor module 2b, for example, among the X-rays generated from the X-ray generating section 1, X-rays having a predetermined amount of X-ray energy in only the necessary X-ray wavelength band, which are different from the X-rays having an amount of X-ray energy in the predetermined wavelength band received at the sensor module 2a, can be obtained.

In this way, by using the X-rays having different predetermined amounts of X-ray energy at the sensor modules 2a, 2b, shadows of the inspected object and the foreign material having different materials can be emphasized.

Note that, the radiation quality of the X-rays of the remaining portion which are not converted to visible light at the sensor module 2a is made to be variable at the sensor module 2b at least.

In this way, the radiation qualities of the X-rays received at the sensor module 2a and the X-rays received at the sensor module 2b are made to be different.

The foreign material detecting operation of the X-ray foreign material detecting apparatus of the above-described structure will be described.

First, X-rays are irradiated from the X-ray generating section 1 onto the inspected object, at a position along the way of the inspected object being conveyed by the conveying section 3.

Accompanying this irradiation of the X-rays, the X-rays transmitted through the inspected object are detected by the respective sensor modules 2a, 2b of the X-ray detecting section 2.

The one sensor module 2a converts a portion of the X-rays transmitted through the inspected object into light by the scintillator 21.

The light converted at the scintillator 21 is reflected in a horizontal direction 90° orthogonal by the visible light reflector 22, and thereafter, is received by the light-receiving element 23.

Here, each photodiode of the light-receiving element 23 converts the received light into an electric signal, and outputs it to a control means (not shown).

Because the light-receiving element 23 is provided at a position at which it does not directly receive the X-rays from the X-ray generating section 1, the durability thereof can be improved.

Further, the X-rays which are not converted into visible light at the sensor module 2a are received at the sensor module 2b.

The radiation quality of these X-rays is changed at the X-ray filter 30, and thereafter, the X-rays are converted into light by the scintillator 31.

The light converted at the scintillator 31 is received by the light-receiving element 33.

Here, each photodiode of the light-receiving element 33 converts the received light into an electric signal, and outputs it to the control means (not shown).

The light-receiving element 33 is provided at a lower position directly receiving the remaining portion of the X-rays from the X-ray generating portion 1, and the received X-rays themselves are damped by the X-ray filter 30. Therefore, the durability thereof can be improved.

The light-receiving elements 23, 33 of the respective sensor units 2a, 2b output X-ray transmission data having different energy amounts corresponding to the portion of the X-rays transmitted through the inspected object and to the remaining portion thereof, respectively.

The control means (not shown) generates an X-ray transmission image having a density gradation corresponding to the X-ray amount of the X-ray transmission data.

Figures 3A, 3B, 3C:
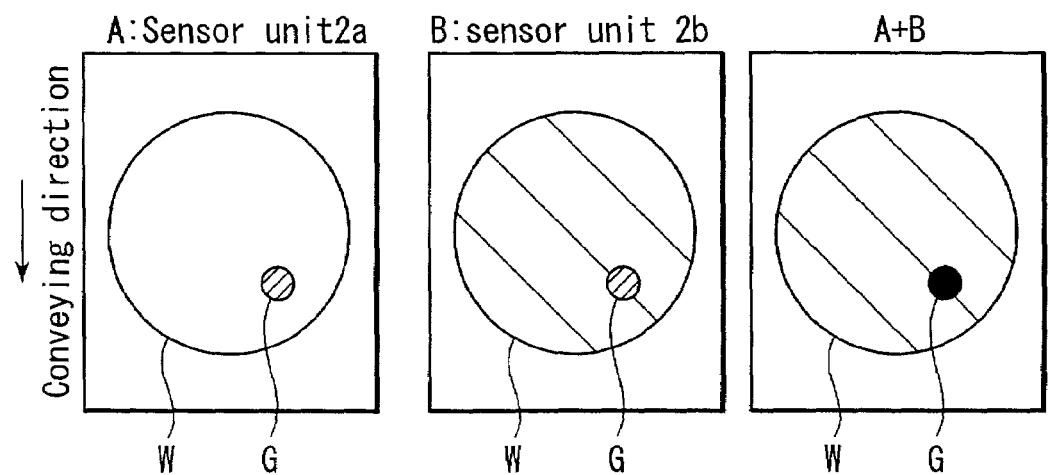
FIGS. 3A, 3B, and 3C are views showing one example of X-ray transmission images of an inspected object W at an X-ray detection signal processing section (not shown) based on a plurality of detection signals by the X-ray foreign material detecting apparatus in accordance with the first embodiment of the present invention.

FIGS. 3A, 3B, and 3C are views showing one example of X-ray transmission images output from the respective sensor units 2a, 2b.

In the example shown in the figure, only the outline of the inspected object is displayed. However, in actuality, the inspected object has a predetermined density in accordance with the X-ray transmission amount.

Further, because the X-ray transmission amount of the foreign material G is small, the density thereof is displayed higher than that of the inspected object W.

Note that, regarding the depiction in the figures of the X-ray transmission amount of the foreign material G, for convenience, a larger number of hatching lines (a higher density) denotes a state in which the X-ray transmission amount is smaller.

The X-ray transmission data output from the one sensor unit 2a is, after image expansion, obtained as an X-ray transmission image A as shown in FIG. 3A.

Further, the X-ray transmission data output from the sensor unit 2b is, after image expansion, obtained as an X-ray transmission image B as shown in FIG. 3B.

As shown in these drawings, when the density of the foreign material G is low (the X-ray transmission amount of the foreign material G is high) in the X-ray transmission image A and the density of the foreign material G is high (the X-ray transmission amount of the foreign material G is low) in the X-ray transmission image B, assuming that (A+B) of these X-ray transmission images A, B is carried out by image processing of the controlling means (not shown), the result is obtained as the image A+B of the state shown in FIG. 3C.

In this way, by making the radiation qualities of the X-rays received at the sensor module 2a and the X-rays received at the sensor module 2b be different from each other at the controlling means (not shown), the density of the foreign material G is made to be relatively high, and the foreign material G is emphasized with respect to the inspected object W, and the foreign material G can be easily extracted.

Further, the image processing of the controlling means (not shown) is not limited to superposing (addition) processing, and difference (subtraction) processing may be executed.

For example, if the difference (B–A) of the X-ray transmission image A from B is executed, the density of the foreign material G is maintained and the density of the inspected object W can be made low. As a result, the foreign material G can be extracted in substantially the same way as in the superposition (A+B).

The above-described two sensor units 2a, 2b are disposed so as to be joined vertically in the transmission direction of the single X-ray beam.

In this way, X-ray foreign material detection of the inspected object W at the same spot is carried out at substantially the same time with respect to the conveying direction of the inspected object W to be conveyed on the conveying section 3.

Accordingly, as shown in FIGS. 3A, 3B, and 3C, an offset in the conveying direction does not arise at the X-ray transmission images A, B in the sensor units 2a, 2b.

Therefore, superposition (or difference) processing of both the image data at the controlling means (not shown) can be easily executed, and electric delay processing or the like for matching both the image data can be rendered unnecessary, and the foreign material G can be easily extracted.

Further, when the inspected object W is deformed while being conveyed, because both of the X-ray transmission images A, B are deformed in the same way in accordance with the deformation, matching of both the images can be aimed for.

At the controlling means (not shown), on the basis of the X-ray transmission data after the above-described image processing, it is determined whether or not there is a foreign material in the inspected object W (including on the surface thereof). A sorting signal or the like showing a good item (there is no foreign material) or a defective item (there is foreign material) from the results of determination is output externally.

Then, the inspected object W, for which the above-described inspection is completed, is conveyed, and thereafter, is sorted into good items or defective items in accordance with the sorting signal output from the controlling means (not shown) by a selector in a later stage or the like.

Further, the X-ray detecting section 2 has the plurality of sensor modules 2a, 2b, but has the single X-ray generating section 1. Therefore, foreign material detection on the basis of X-rays having different radiation qualities can be carried out even if the plurality of the X-ray generating section 1 and the X-ray detecting section 2 are not provided. Therefore, the above-described foreign material detection can be carried out while suppressing an increase in costs.

Next, a concrete example of foreign material detection by the plurality of sensor modules 2a, 2b described above will be explained.

At the one sensor module 2a, because there is no X-ray filter 30, X-rays whose transmission amount is not damped are received. The sensor module 2a outputs an electric signal corresponding to the transmission amount of these X-rays to the controlling means (not shown).

Further, at the sensor module 2b at which the X-ray filter 30 is provided, X-rays whose transmission amount is damped are received. The sensor module 2b outputs an electric signal corresponding to the transmission amount of these X-rays to the controlling means (not shown).

In concrete examples, cases can be considered in which a bone, a shell or the like which is originally there in processed food, or metal or the like which should not be originally there in processed food are detected as foreign material G in the inspected object W (including on the surface thereof) which is processed food.

In this case, only metal, through which it is difficult for X-rays to be transmitted, is emphasized in the X-ray transmission data output at the sensor module 2a at which the X-rays whose transmission amount is not damped are received.

Then, the X-ray filter 30 damps the X-ray energy amount only in a predetermined wavelength band at which the X-ray energy is high among the X-rays generated from the X-ray generating section 1. Thus, at the controlling means (not shown), the shadows of a soft material in the inspected object W and the foreign material G can be emphasized.

Further, on the basis of the X-ray transmission data of the sensor module 2b which receives the X-rays from which the portion having a high X-ray energy amount has been deleted by the X-ray filter 30 (namely, a low X-ray energy amount), at the controlling means (not shown), bones and shells and the like (small foreign materials and thin foreign materials) through which it is easy for the X-rays to be transmitted, can also be emphasized.

In this way, at the controlling means (not shown), due to a plurality of threshold values being set in accordance with the type of the desired foreign material G with respect to both X-ray transmission data from the sensor module 2a and the sensor module 2b, it can be determined whether the foreign material in the inspected object W selected as a defective item is only bone, shell or the like (a small foreign material or a thin foreign material), or is only metal or the like, or includes both bone, shell or the like (a small foreign material or a thin foreign material) and metal or the like. A determination signal can be output externally in addition to the above-described sorting signal for a good item and a defective item.

For example, it can be supposed that bone, metal, or the like as the type of the foreign material G is mixed in the food of ham serving as the inspected object W, and inspection can be carried out including inspection per type of the foreign materials G.

Accordingly, due to the above-described X-ray foreign material detecting apparatus having the sensor modules 2a, 2b which receive X-rays of different radiation qualities, it is possible to individually detect foreign material through which X-rays are easily transmitted (small foreign materials or thin foreign materials such as bones and shells), and foreign material through which it is difficult for X-rays to be transmitted (metal and the like). Thus, highly-accurate foreign material detection can be carried out without limiting the properties of the foreign material to be detected.

Further, it goes without saying that, by subjecting both X-ray transmitted images to the above-described superposing or difference processing at the control means (not shown) as described above, extracting processing, such as emphasizing the foreign material G relatively with respect to the inspected object W, can be carried out.

Note that, as shown by the broken line in FIG. 2, the X-ray filter 30 may be provided at the sensor unit 2a, and not at the sensor unit 2b.

(Second Embodiment)

The above-described first embodiment is a case in which, as shown in FIG. 2, the radiation quality of the X-rays is changed by providing the X-ray filter 30 at the one sensor unit 2b.

A second embodiment is a case of a structure (not shown) using members having respectively different X-ray/light conversion characteristics as the scintillators 21, 31 provided at the sensor units 2a, 2b, without providing the X-ray filter 30 at the sensor unit 2b.

In this way, in the second embodiment, the sensor units 2a, 2b can respectively detect X-ray transmission amounts having different X-ray wavelength bands, i.e., energy amounts. Thus, even if the X-ray filter 30 is not used, in the same way as in the case of using the X-ray filter 30, it is possible to detect different types of foreign materials at the respective sensor units 2a, 2b.

Further, due to the superposition processing or the difference processing of the X-ray transmitted images by the control means (not shown), the foreign material G can be emphasized relatively with respect to the inspected object W.

(Third Embodiment)

Figure 4:
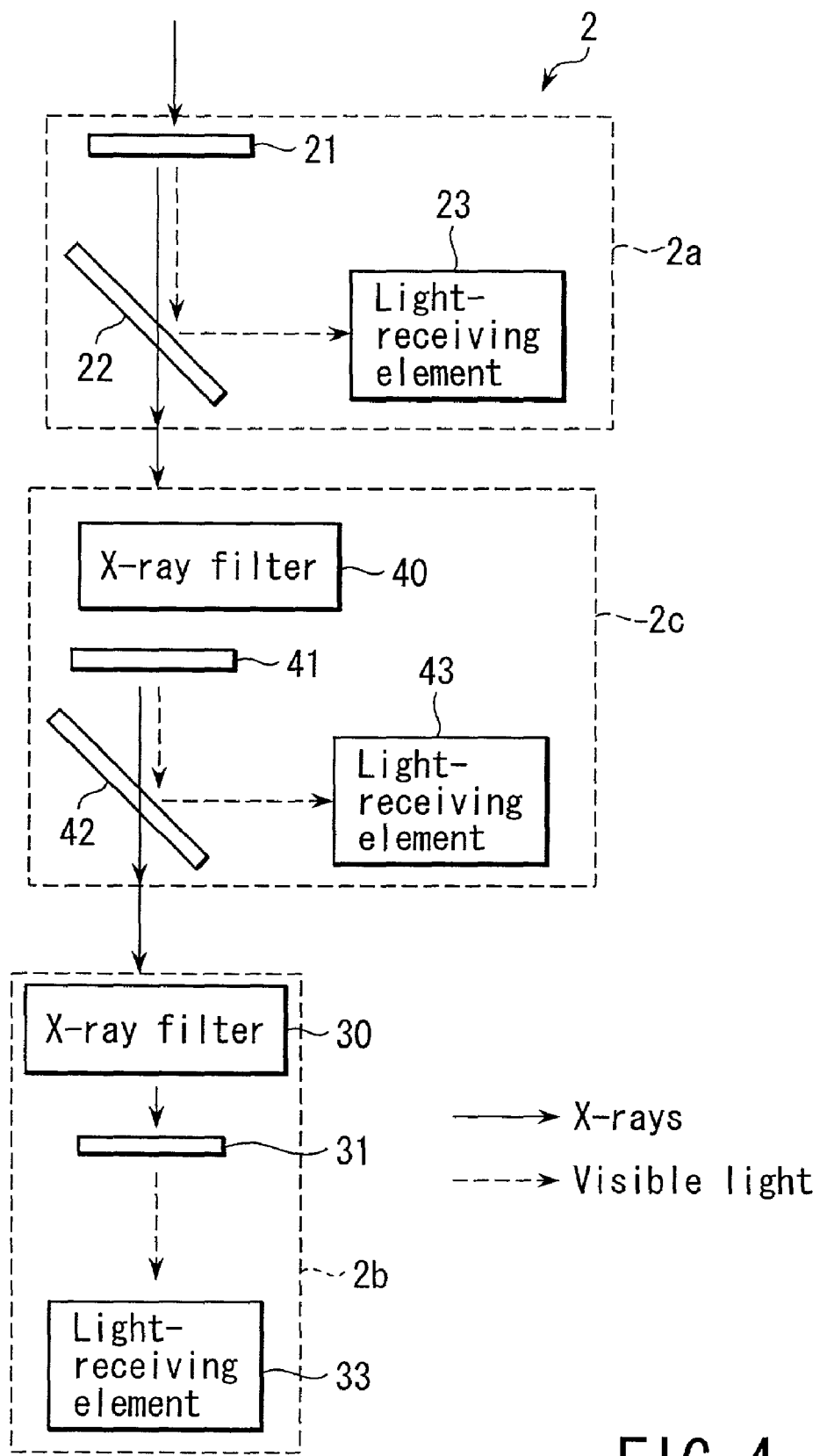
FIG. 4 is a diagram showing an inner structure of the X-ray detecting section 2 of FIG. 1, as a schematic diagram showing main portions of an X-ray foreign material detecting apparatus in accordance with a third embodiment of the present invention.
Figure 5:
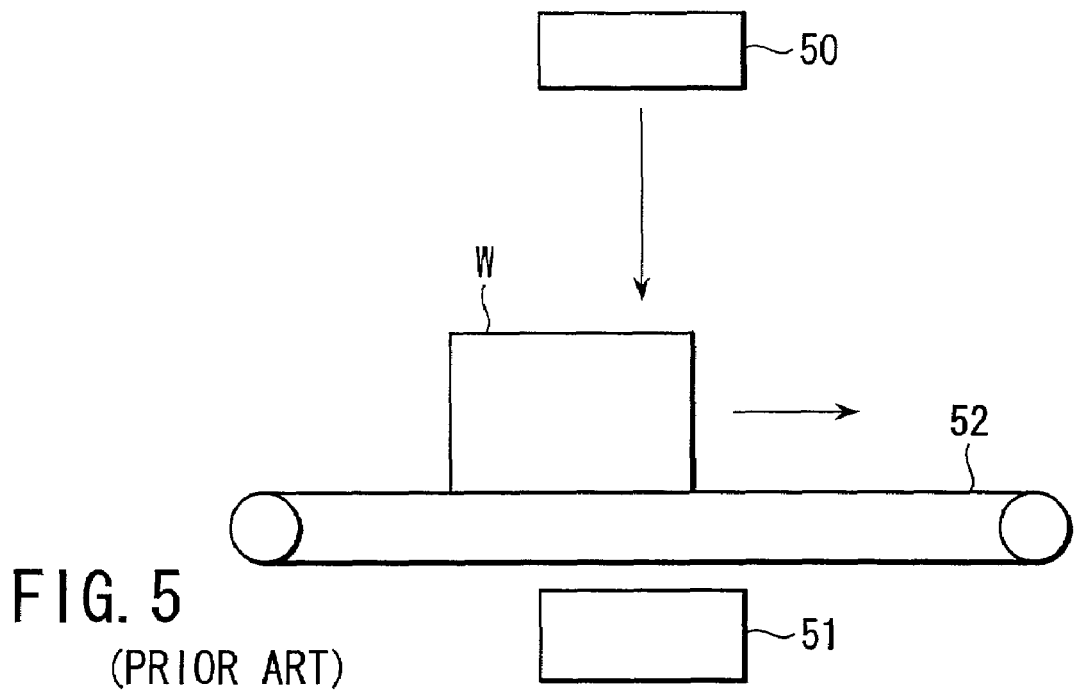
FIG. 5 is a schematic diagram showing a structure of a conventional X-ray foreign material detecting apparatus.

FIG. 4 is a diagram showing an internal structure of an X-ray detecting section 2, as a schematic diagram showing the structure of main portions of the X-ray foreign material detecting apparatus in accordance with a third embodiment of the present invention.

Namely, as shown in FIG. 4, the X-ray foreign material detecting apparatus in accordance with the third embodiment of the present invention is a case in which three sensor modules 2a, 2b, and 2c are provided at the X-ray detecting portion 2.

These sensor modules 2a, 2b, and 2c are respectively disposed so as to be connected in the vertical direction so as to receive a single X-ray beam irradiated from the X-ray generating section 1.

In this case, the uppermost and lowermost sensor modules 2a, 2b are structured in the same way as the sensor modules 2a, 2b in the above-described first embodiment.

Further, the sensor module 2c provided in the middle is a structure combining the sensor module 2a and the sensor module 2b.

Namely, as shown in FIG. 4, an X-ray filter 40, a scintillator 41, a visible light reflector 42, and a light-receiving element 43 are provided at the sensor module 2c.

Here, filters which change the X-rays to have respectively different radiation qualities are used as the X-ray filters 40, 30 provided at the middle and lowermost sensor modules 2c, 2b.

Concretely, X-ray filters 40, 30 (which may be partially superposed) are used in which the predetermined wavelength band, i.e., energy amount, of the X-rays damped by at least the lowermost X-ray filter 30 is different than the predetermined wavelength band, i.e., energy amount, of the X-rays damped by the intermediate X-ray filter 40.

The radiation quality, with respect to the remaining portion of the X-rays not converted into visible light at the uppermost sensor module 2a, is variable at the intermediate sensor module 2c.

Further, the radiation quality, with respect to the remaining portion of the X-rays which are not converted into visible light at the uppermost sensor module 2a and the intermediate sensor module 2c, is variable at the lowermost sensor module 2b.

In this way, the radiation qualities of the X-rays received at the respective sensor modules 2a, 2b, and 2c are all different.

In this way, in the present invention, by providing the sensor modules in plural stages of two or more stages vertically and by making the radiation qualities of the X-rays differ at each of the sensor modules 2a, 2b, and 2c, foreign materials G of different types can be emphasized and detected in accordance therewith.

Further, in the present invention, the further a position is toward the lowermost sensor module, the more the X-ray energy amount received by the sensor module is damped. Thus, even if the foreign material G is a soft material, it is emphasized and can be detected.

Note that, even if the sensor modules are provided in plural stages of two or more stages, all receive a single X-ray beam. Thus, because the same spot of the inspected object W conveyed by the conveying section 3 can always be detected simultaneously, image processing in the controlling means (not shown) can be easily carried out.

As described above, in the X-ray foreign material detecting apparatus in accordance with the present invention, due to a plurality of sensor modules being disposed vertically along the irradiating direction of a single X-ray beam and due to providing an X-ray filter at the desired sensor module, the respective sensor modules can simultaneously receive X-rays having different radiation qualities, and a foreign material in the inspected object can be precisely detected by a simple structure.

At this time, because the respective sensor modules always output the X-ray transmission data regarding the same spot such that the same spot of the inspected object is detected at the same detection time, image processing such as superposition, difference, and the like using image data after expansion can be easily carried out, and the precision of detecting a foreign material can be easily improved.

Further, because the respective sensor modules can detect individual foreign materials mixed in the inspected object such as a foreign material through which X-rays are easily transmitted, a foreign material through which it is difficult for X-rays to be transmitted, and the like, the foreign material to be detected is not limited, and precise foreign material detection can be carried out.

Further, due to the structure in which a light reflector is provided in the module and a light-receiving element is set apart from the irradiating direction of the X-rays, the durability of the light-receiving element can be improved.

Further, due to the structure in which sensor modules respectively have scintillators having different light-converting characteristics, different foreign materials can be detected without providing an X-ray filter.

Further, in accordance with the X-ray foreign material detecting apparatus of the present invention, by using the structure in which various types of foreign materials are detected on a manufacturing line or the like in which a conveying section sequentially conveys inspected objects, foreign material detection can be simultaneously carried out at the respective sensor modules while changing the radiation qualities. Thus, real-time and highly-precise foreign material detection can be carried out, and the effect that performance of the entire apparatus can be improved is obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray foreign material detecting apparatus comprising:
   an X-ray generating section which irradiates a predetermined energy amount of X-rays at a single irradiation time;
   a conveying section which successively conveys an inspected object at a predetermined speed so as to cross the predetermined energy amount of X-rays irradiated at the singe irradiation time from the X-ray generating section, the inspected object including an object which is successively produced and may be changed in shape during conveyance;
   a first scintillator disposed along a transmitting direction of the X-rays transmitted through the inspected object successively conveyed by the conveying section at a predetermined speed, which converts to light, one portion of transmitted X-rays transmitted through the inspected object, obtained by exposing the predetermined energy amount of X-rays at the single irradiaton time, from the X-ray generating section to the inspected object which is being conveyed at the predetermined speed by the conveying section;
   a first visible light reflector which reflects the light converted by the first scintillator;
   a first sensor module which includes a first light receiving element for receiving the light reflected by the first visible light reflector, and outputs a first electric signal corresponding to a first X-ray energy amount that the one portion of the transmitted X-rays has by using the one portion of the transmitted X-rays transmitted through the inspected object;
   first X-ray energy amount converting means which is disposed under the first sensor module along a transmitting direction of the X-rays transmitted through the inspected object successively conveyed by the conveying section at a predetermined speed, which receives a remaining portion of the transmitted X-rays transmitted through the inspected object excluding the one portion of the transmitted X-rays received by the first sensor module, obtained by exposing the predetermined X-ray energy amount of X-rays during the single irradiation time from the X-ray generating section to the inspected object which is being conveyed at a predetermined speed by the conveying section and converts into X-rays having a second X-ray energy amount different by a predetermined magnitude fro the first X-ray energy amount by using the remaining portion of the transmitted X-rays transmitted through the inspected object;
   a second scintillator which is disposed under the first X-ray energy amount converting means along a transmitting direction of the X-rays transmitted through the inspected object successively conveyed by the conveying section at a predetermined speed, which converts to light, the X-rays having the second X-ray energy amount converted by the first X-ray energy amount converting means;
   a second visible light reflector which reflects the light converted by the second scintillator;
   a second sensor module which includes a second light receiving element for receiving the light reflected by the second visible light reflector, and outputs a second electric signal corresponding to a second X-ray energy amount different from the first X-ray energy amount, at substantially the same time as the first electric signal output from the first sensor module, by using the X-rays having the second X-ray energy amount;
   second X-ray energy amount converting means which is disposed under the second sensor module along a transmitting direction of the X-rays transmitted through the inspected object successively conveyed by the conveying section at a predetermined speed, which receives a remaining portion of the transmitted X-rays transmitted through the inspected object excluding the one portion of the transmitted X-rays received by the first and second sensor modules, obtained by exposing the predetermined X-ray energy amount of X-rays during the single irradiation time, from the X-ray generating section to the inspected object which is being conveyed at a predetermined speed by the conveying section and converts into X-rays having a third X-ray energy amount different by a predetermined magnitude from the first X-ray energy amount and the second X-ray energy amount by using the remaining portion of the transmitted X-rays transmitted through the inspected object;
   a third scintillator which is disposed under the second X-ray energy amount converting means along a transmitting direction of the X-rays transmitted through the inspected object successively conveyed by the conveying section at a predetermined speed, which converts to light, the X-rays having the third X-ray energy amount converted by the first X-ray energy amount converting means; and
   a third sensor module which includes a third light receiving element for receiving the light converted by the third scintillator, and outputs a third electric signal corresponding to a third X-ray energy amount different from the first X-ray energy amount and the second X-ray energy amount, at substantially the same time as the first and second electric signals output from the first and second sensor modules, by using the X-rays having the third X-ray energy amount;
   wherein presence/absence of a foreign material mixed in the inspected object, successively conveyed by the conveying section at a predetermined speed can be detected at high speed with high accuracy irrespective of a change in shape of the inspected object during conveyance, in accordance with the first electric signal, the second electric signal and the third electric signal, respectively corresponding to the first X-ray energy amount, the second X-ray energy amount which is different from the first X-ray energy amount and the third X-ray energy amount which is different from the first X-ray energy amount and the second X-ray energy amount, which are output from the first, second and third sensor modules with respect to the same portion of the same inspected object at substantially the same detection time.

2. The X-ray foreign material detecting apparatus according to claim 1, wherein at least one of the first and second sensor modules has a first X-ray filter serving as the first X-ray energy amount converting means to make the first X-ray energy amount and the second X-ray energy amount different from each other by a predetermined magnitude by using the one portion or the remaining portion excluding the one portion of the transmitted X-rays transmitted through the inspected object, and at least one of the second X-ray energy amount converting means to make the third X-ray energy amount different from the first X-ray energy amount and the second X-ray energy amount by a predetermined magnitude by using the one portion or the remaining portion excluding the one portion of the transmitted X-rays transmitted through the inspected object.

3. An X-ray foreign material detecting method comprising:

irradiating a predetermined X-ray energy amount of X-rays at a single irradiation time;

successively conveying an inspected object at a predetermined speed so as to cross the predetermined X-ray energy amount of X-rays irradiated at the single irradiation time, the inspected object including an object which is successively produced and may be changed in shape during conveyance;

receiving one portion of transmitted X-rays transmitted through the inspected object successively conveyed at the predetermined speed, obtained by exposing the predetermined X-ray energy amount of X-rays at a single irradiation time, to the inspected object which is successively conveyed at the predetermined speed, converting the one portion of the transmitted X-rays transmitted through the inspected object to a first visible light, reflecting the first visible light to a sensor module, and outputting a first electric signal corresponding to a first X-ray energy amount that the one poriton of the transmitted X-rays has;

receiving a remaining portion of the transmitted X-rays transmitted through the inspected object, excluding the one portion of the transmitted X-rays, obtained by exposing a predetermined X-ray energy amount of X-rays at the single irradiation time to the inspected object which is successively conveyed at the predetermined speed by a first X-ray energy amount converter disposed under the first sensor module along a transmitting direction of the X-rays transmitted through the inspected object conveyed successively at the predetermined speed, and converting the remaining portion of the transmitted X-rays transmitted through the inspected object into X-rays having a second X-ray energy amount different by a predetermined magnitude from the first X-ray energy amount;

receiving the X-rays having the second X-ray energy amount converted by the first X-ray energy amount converter, converting the X-rays having the second X-ray energy amount to a second visible light, reflecting the second visible light to a sensor module, and outputting a second electric signal corresponding to a second X-ray energy amount at substantially the same time as the first electrical signal output from the first sensor module;

receiving the remaining portion of the transmitted X-rays transmitted through the inspected object excluding the one portion of the transmitted X-rays received by the first and second sensor modules obtained by exposing the predetermined X-ray energy amount of X-rays during the single irradiation time to the inspected object which is being conveyed at a predetermined speed, by a second X-ray energy amount converter which is disposed under the second sensor module along a transmitting direction of the X-rays transmitted through the inspected object sucessively conveyed at a predetermined speed and converting the remaining portion of the transmitted X-rays transmitted through the inspected object into X-rays having a third X-ray energy amount different by a predetermined magnitude from the first X-ray energy amount and the second X-ray energy amount; and converting the X-rays having the third X-ray energy amount to a third visible light;

and outputting a third electric signal corresponding to the third X-ray energy amount at substantially the same time as the first and second electric signals output from the first and second sensor modules by using the X-rays having the third X-ray energy amount, wherein the presence/absence of a foreign material mixed in the inspected object successively conveyed at a predetermined speed can be detected at a high speed with high accuracy irrespective of a change in shape of the inspected object during conveyance, in accordance with the first electric signal, the second electric signal and the third electric signal, respectively corresponding to the first X-ray energy amount, the second X-ray energy amount which is different from the first X-ray energy amount and the third X-ray energy amount which is diffferent from the first X-ray energy amount and the second X-ray energy amount, which are output from the first, second and third sensor modules about the same inspected object at substantially the same direction time.

4. An X-ray foreign material detecting method comprising:

irradiating a predetermined X-ray energy amount of X-rays at a single irradiation time;

successively conveying an inspected object at a predetermined speed so as to cross the predetermined X-ray energy amount of X-rays irradiated at the single irradiation time, the inspected object including an object which is successively produced and may be changed in shape during conveyance;

converting one portion of transmitted X-rays transmitted through the inspected object and obtained by exposing a predetermined X-ray energy amount of X-rays at the single irradiation time to the inspected object which is being successively conveyed at a predetermined speed into a first visible light;

reflecting the first visible light;

receiving the first visible light, and outputting a first electric signal corresponding to a first X-ray energy amount that the one portion of the transmitted X-rays has;

converting X-rays which have a second X-ray energy amount different from the first X-ray energy amount by a predetermined magnitude, a remaining portion of the transmitted X-rays transmitted through the inspected object, excluding the one portion of the transmitted X-ray having the first X-ray energy amount and obtained by exposing a predetermined X-ray energy amount of X-rays at the single irradiation time to the inspected object which is being successively conveyed at a predetermined speed;

converting the X-rays which have the second X-ray energy amount into a second visible light;

reflecting the second visible light;

receiving the second visible light, and outputting a second electric signal corresponding to a second X-ray energy amount at substantially the same time as the first electric signal;

converting a remaining portion of the transmitted X-rays transmitted through the inspected object excluding the one portion of the transmitted X-rays having the first energy amount and the second energy amount obtained by exposing the predetermined X-ray energy amount of X-rays during the single irradiaton time to the inspected object which is being successivley conveyed at a predetermined speed into X-rays having a third X-ray energy amount which is different by a predetermined magnitude from the first X-ray energy amount and the second X-ray energy amount;

converting the X-rays having the third X-ray energy amount into a third vissible light; and receiving the third visible light, and outputting a third electric signal corresponding to the third X-ray energy amount at substantially the same time as the first and second electric signals;

wherein the presence/absence of a foreign material mixed in the inspected object being successively conveyed at a predetermined speed can be detected at high speed with high accuracy irrespective of a change in shape of the inspected object during conveyance, in accordance with the first electric signal and the second electric signal, respectively corresponding to the first X-ray energy amount and the second X-ray energy amount different from the first X-ray energy amount, and the third electric signal corresponding to the third X-ray energy amount different from the first X-ray energy amount and the second X-ray energy amount which are output with respect to the same portion of the same inspected object at substantially the same detection time.

* * * * *